United States Patent
Marquiss

(10) Patent No.: US 8,577,116 B2
(45) Date of Patent: Nov. 5, 2013

(54) ASSAY IMAGE ACQUISITION SYSTEM AND METHOD

(75) Inventor: Samuel Ascher Marquiss, Santa Clara, CA (US)

(73) Assignee: Molecular Devices, LLC, Sunnyvale, CA (US)

( * ) Notice: Subject to any disclaimer, the term of this patent is extended or adjusted under 35 U.S.C. 154(b) by 156 days.

(21) Appl. No.: 13/363,709

(22) Filed: Feb. 1, 2012

(65) Prior Publication Data

US 2013/0195344 A1    Aug. 1, 2013

(51) Int. Cl.
*G06K 9/00*      (2006.01)
*G01C 3/08*      (2006.01)

(52) U.S. Cl.
USPC .......................... 382/133; 382/274; 356/3.02

(58) Field of Classification Search
USPC ......... 382/100, 103, 107, 128–134, 162, 168, 382/173, 181, 199, 203, 209, 219, 232, 254, 382/274–275, 276, 291, 294, 305, 312; 422/505; 356/512, 3.02; 703/5; 250/201.3; 348/222.1; 702/186
See application file for complete search history.

(56) References Cited

U.S. PATENT DOCUMENTS

| | | | | |
|---|---|---|---|---|
| 6,902,703 B2 * | 6/2005 | Marquiss et al. | ............. | 422/505 |
| 7,557,932 B2 * | 7/2009 | Doan et al. | ................... | 356/512 |
| 8,447,569 B1 * | 5/2013 | Marwah et al. | ............... | 702/186 |
| 8,484,000 B2 * | 7/2013 | Gulati | ............................... | 703/5 |
| 2006/0192076 A1 * | 8/2006 | Ishida et al. | ............... | 250/201.3 |
| 2011/0249137 A1 * | 10/2011 | Suzuki et al. | ............. | 348/222.1 |

* cited by examiner

*Primary Examiner* — Seyed Azarian
(74) *Attorney, Agent, or Firm* — Bella Fishman

(57) ABSTRACT

A computer-implemented method of imaging an assay sample having a set of individual samples using a camera is provided. A set of image frames is received. The set of image frames corresponds to an image stream of the assay obtained by the camera. A set of measurement results is identified. Individual measurement results in the set of measurement results are respectively associated with individual image frames in the set of image frames. A subset of measurement results is selected based, at least in part, on an exposure time. Individual measurement results in the subset of measurement results are combined to obtain an integrated measurement result.

18 Claims, 6 Drawing Sheets

ASSAY IMAGE ACQUISITION SYSTEM AND METHOD

FIELD OF THE INVENTION

This invention relates to systems and methods for conducting and measuring biological assays.

BACKGROUND

During a biological assay researchers may use a camera to capture images of cell responses during the data acquisition phase. One type of biological assay may measure the response of cardiac muscle cells (cardiomyocytes) to potential drug compounds. This type of cardiomyocyte assay may load cardiomyocyte cells with a calcium dye, add a potential drug compound, and measure, for example, the changing spectral properties (e.g., fluorescence or luminescence) of the calcium dye due to biological activity at the cardiomyocytes.

Assaying cardiomyocytes may involve monitoring changes to the concentration gradient of calcium ions across a cardiomyocyte membrane that result in changes to the membrane voltage potential for the cardiomyocyte. A cardiomyocyte assay may monitor the flux of calcium ions into and out of a cardiomyocyte using the calcium dye. The calcium dye may have spectral properties, e.g., fluorescent or luminescent properties that change in the presence of calcium ions. Accordingly, light may serve as a proxy for calcium flux.

A camera, as mentioned above, may capture images of the cardiomyocytes during the assay to monitor the changes in the light from the calcium dye. Researchers may then analyze the image data to determine the effects of potential drug compounds on the cardiomyocytes.

The camera may be capable of capturing images at a relatively high frame rate, e.g., 120 frames per second (fps). Overhead, however, may limit the effective frame rate of the camera when processing the image data.

As an example, a camera may take a 0.05 second (sec.) exposure of a biological assay sample during a 0.125 second interval period. Part of the interval period, e.g., 0.075 seconds, may be devoted to software overhead that includes image data handling and transmission. As a result, the exposure time and overhead that comprise the interval period may limit the effective frame rate of the camera to 1÷(exposure time+overhead) frames per second.

Using the example above, the effective frame rate for a 0.05 sec. exposure and 0.075 sec. overhead is 8 fps: 1÷(0.05+0.075)=1÷0.125=8 fps. Thus the overhead inhibits utilization of the camera maximum frame rate, e.g., 120 fps. Relevant biological activity, however, may occur during the overhead period—in other words, between exposures—and fail to be captured by the camera. Attempting to use the maximum frame rate despite the overhead shortens the available exposure time. A short exposure time may result in an image signal too dim to produce an adequate image of the assay sample. Accordingly, the effective frame rate of the camera may also be inhibited by the need for an exposure time long enough to produce an adequate image.

Therefore a need exists for a new approach to imaging biological assays that can take advantage of the high-speed capabilities of the imaging camera.

SUMMARY

A computer-implemented method of imaging an assay sample having a set of individual samples using a camera is provided. A set of image frames is received. The set of image frames corresponds to an image stream of the assay obtained by the camera. A set of measurement results is identified. Individual measurement results in the set of measurement results are respectively associated with individual image frames in the set of image frames. A subset of measurement results is selected based, at least in part, on an exposure time. Individual measurement results in the subset of measurement results are combined to obtain an integrated measurement result.

A system for imaging an assay sample having a set of individual samples using a camera is also provided. An image processing module receives a set of image frames. The set of image frames corresponds to an image stream of the assay sample obtained by the camera. Individual image frames in the set of image frames respectively correspond to individual measurement results in a set of measurement results. The image processing module selects a subset of measurement results from the set of measurement results based, at least in part, on an exposure time. The image processing module also combines individual measurement results in the subset of measurement results to obtain an integrated measurement result.

A computer-implemented method of imaging an assay sample having a set of individual samples using a camera is further provided. An image stream of the assay sample is obtained during an imaging period with the camera. The image stream of the assay sample obtained during the imaging period is stored. The stored image stream is sampled at the conclusion of the imaging period to obtain a set of image frames. The image frames correspond to the stored image stream. One or more image correction operations are performed on individual image frames in the set of image frames to obtain a set of corrected image frames. The set of corrected image frames is converted to obtain a set of measurement results. A subset of measurement results is selected from the set of measurement results based, at least in part, on an exposure time. Individual measurement results in the subset of measurement results are combined to obtain an integrated measurement result.

DETAILED DESCRIPTION

A system and method for imaging biological assays are provided. A high-speed camera images an assay sample at a relatively high frame rate, e.g., 120 fps. As the camera images the assay sample, the camera generates an image stream. During the imaging period, the camera collects the image stream as raw image data. The images are then corrected (e.g., flat-fielded) and converted to intensity values for each well location in order to reduce the data size. The image data is then stored as the system continues to obtain the raw data. As discussed further below, image exposures are artificially recreated for a particular exposure time (e.g., 0.05 seconds) by integrating image-related information associated with the raw image frames corresponding to the particular exposure period. By storing the image stream for the duration of the imaging period, sampling the raw image data at the conclusion of the imaging period, and artificially recreating image exposures, overhead associated with the imaging process may be avoided thereby avoiding gaps in the image stream during image acquisition.

Figure 1:
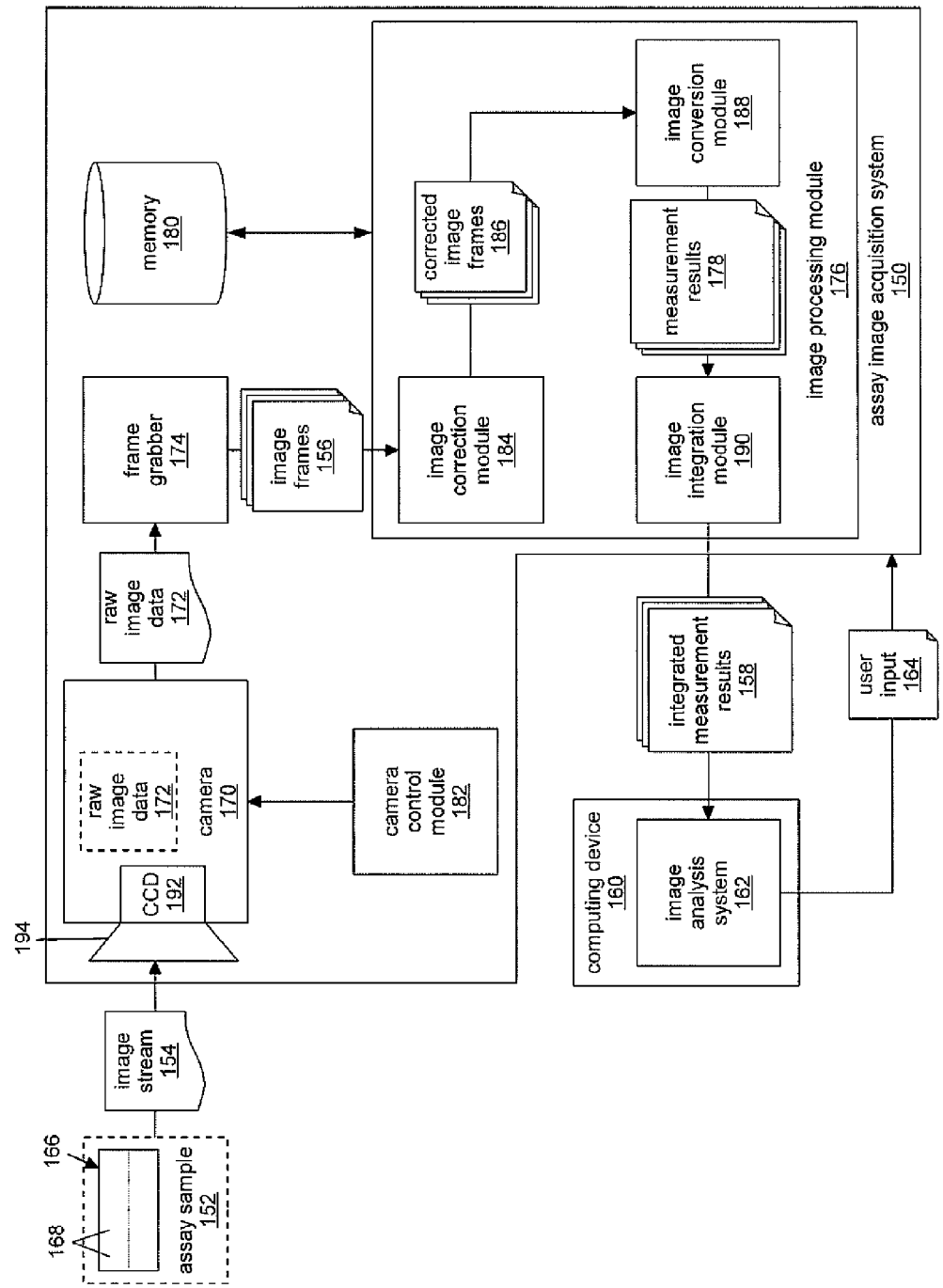
FIG. 1 is an example of an implementation of an assay image acquisition system.

Referring to FIG. 1, an example of an implementation of an assay image acquisition system 150 is shown. The assay image acquisition system 150, in this example, may image an assay sample 152 to obtain an image stream 154 and artificially recreate image exposures from image frames 156 that correspond to the image stream 154. The assay image acquisition system 150 may generate integrated measurement results 158 based on the image frames. The assay image acquisition system 150 may be in signal communication with a computing device 160 that includes an image analysis system 162, and the assay image acquisition system 150 may transmit the integrated measurement results 158 to the image analysis system 162 for further processing and analysis. The assay image acquisition system 150 may also receive user input 164 from the image analysis system 162. The user input 164 may control the operation of the assay image acquisition system 150 as discussed further below.

The assay sample 152, in this example, may include a microplate 166 having an array of wells 168 that respectively hold individual samples for assaying. The individual samples in the assay sample 152 respectively correspond to individual locations in the assay sample 152. The microplate 166 may be a standard microplate having, for example, 96, 384, or 1536 total wells 168. An image frame 156 of the microplate 166 may include an array of subsections where individual subsections of the image frame 156 correspond to one of the wells 168 in the microplate 166, i.e., one of the locations in the assay sample 152. For example, a microplate 166 having a two-dimensional array of 96 total wells 168 may correspond to an image frame 156 having a two-dimensional array (e.g., 8×12) of 96 total subsections. An image frame 156, and by extension the subsections of an image frame 156, may be comprised of image data, e.g., a two-dimensional pixel array. Pixels in the pixel array may be specified, for example, as a grayscale (monochromic) value. The grayscale values may, for example, be integer values and range, e.g., from 0 to 255, with black corresponding to a grayscale value of 0, white corresponding to a grayscale value of 255, and varying levels of gray corresponding to values between 0 and 255. It will be understood that alternative ranges may be selectively employed for the grayscale values in order to identify more or less grayscale levels.

The image analysis system 162 may reside at a computing device 160 such as, for example, a desktop computer, a laptop computer, a tablet computer, a mobile telephone, and the like. The image analysis system 162 may be implemented using, for example, the ScreenWorks® system control software available from Molecular Devices, LLC of Sunnyvale, Calif., or any other suitable image analysis system. As discussed further below, the image analysis system 162 may present a graph of the integrated measurement results 158 to illustrate how the integrated measurement results 158 change during the imaging period. The image analysis system 162 may be in signal communication with the assay image acquisition system 150 via any suitable electronic communication link such as, for example, a wired communication link, e.g., Ethernet, USB (Universal Serial Bus), FireWire, and the like; or a wireless communication link, e.g., Wi-Fi, Bluetooth, and the like. The image analysis system 162 may also be in signal communication with the assay image acquisition system 150 via a network such as, for example, the Internet.

The assay image acquisition system 150, in this example, includes: a camera 170 that acquires an image stream 154 of the assay sample 152; a frame grabber 174 that samples the raw image data 172 to obtain a set of image frames 156; and an image processing module 176 that generates a set of integrated measurement results 158.

Measurement results 178 may include, for example, numerical values. A numerical value may correspond, for example, to a property of an assay sample location such as, for example, fluorescence or luminescence of an individual cardiomyocyte assay sample as discussed above. Accordingly the measurement results 178 may quantify a physical property of the individual samples in the assay sample 152.

The assay image acquisition system 150 may also include, as shown by way of example in FIG. 1: a memory 180 that stores the measurement data and a camera control module 182 that controls the operation of the camera 170. The image processing module 176 may include, as shown by way of example in FIG. 1: an image correction module 184 that performs a set of image correction operations on the image frames 156 to obtain a set of corrected image frames 186; an image conversion module 188 that converts the corrected image frames 186 (or image frames 156) to a set of numerical values representing the measurement results 178; and an image integration module 190 that integrates measurement results 178 to obtain integrated measurement results 158.

The camera 170 may be, for example, a "high-speed" camera capable of acquiring an image stream 154 at a relatively high frame rate, e.g., 120 fps. The camera 170 may also be a CCD camera, i.e., a camera that uses a charge-couple device 192 as an image sensor. Additionally, the CCD of the camera 170 may include an image intensifier 194 such that the charge-couple device 192 is an ICCD—intensified charge-couple device. Where the CCD 192 of the camera includes an image intensifier 194, the camera 170 may be referred to as an ICCD camera. The image intensifier 194 may magnify the effect of any light emitted by individual samples of the assay sample 152 during the imaging period. In this way, the assay image acquisition system 150 may advantageously capture relatively faint emissions of light from the assay sample 152. Other high-speed cameras may be selectively employed such as, for example, a scientific CMOS camera from Andor Technology headquartered in Belfast, Northern Ireland.

A suitable high-speed camera 170 may be available, for example, from Stanford Photonics, Inc. of Palo Alto, Calif.

The camera control module 182 may control operation of the camera 170. The camera control module 182, in this example, receives low-level commands from the software controlling the assay image acquisition system 150. The commands may control, for example, various camera parameters such as intensifier gain and temperature. The user may set the gain using the image analysis system 162, which may then transmit this information to the assay image acquisition system 150 as user input 164.

As mentioned above, the camera 170 may acquire an image stream 154 during the image acquisition period of the assay. During the image acquisition period, a frame grabber 174 generates a set of image frames 156. The frame grabber 174 is an electronic component that captures individual still image frames from an analog video signal or digital video stream.

An image frame 156, in this example, may have a relatively low resolution, e.g., 640 pixels by 480 pixels (640×480). As mentioned above an image frame 156 may include multiple subsections that respectively correspond to a particular location in the assay sample 152, e.g., a particular well 168 in the microplate 166. The resolution of the subsection may depend on the number of sample locations in the assay sample 152, e.g., the number of wells 168 in the microplate 166. A well having 384 total wells in a 2:3 arrangement, i.e., 16 wells by 24 wells, may, for example, correspond to a 640×480 image frame 156 having 384 subsections with respective resolutions of around 40×20 pixels: 640÷16=40 pixels and 480÷24=20 pixels. It will be understood that additional or alternative image resolutions may selectively be employed.

The image correction module 184, in this example, performs image correction operations on the image frames 156 to obtain a set of corrected image frames 186. The image correction module 184 may perform correction operations on the image frames 156 to calibrate the image frames 156 before additional processing such as, for example, conversion of an image frame 156 to a set of numerical values. Correction operations may include, for example, flat-field correction, analog-to-digital conversions (ADC) offset, and background subtraction. Flat-field correction provides a uniform output for a uniform input, correcting for uneven illumination and lens roll-off (i.e., vignetting), and ADC offset corrects for data offsets.

The image conversion module 188 may receive the corrected image frames 186 (or the image frames 156 if image correction is omitted) for conversion. The image conversion module 188, in this example, converts a corrected image frame 186 to a set of numerical values by processing the image data of the image frame 186 to generate the set of numerical values. The set of numerical values may be, for example, a data table, a data matrix, and the like. Individual entries in the data table may respectively correspond to a subsection of the image frame 186 and, by extension, one of the locations in the assay sample 152. Accordingly when converting a subsection of the image frame 186 to a numerical value, the image conversion module 188 may, for example, select a subset of image data from the image frame 186, e.g., a 40×20 subset of pixel data that corresponds to the subsection being converted into a numerical value.

A numerical value may be a value that corresponds to a property of an individual sample in the assay sample 152. For example, the numerical value may correspond to the fluorescence or luminescence (light intensity) of an individual sample of the assay sample 152. Accordingly the image conversion module 188 may, as an example, convert an image frame 186 to a data table of light intensity values where individual light intensity values respectively correspond to a subsection of the image frame 186 and, by extension, one of the wells 168 of the microplate 166.

The image conversion module 188 may convert the subsection of the image frame 186 to a numerical value based on the image data (e.g., pixel values) in the subsection. The numerical values may be referred to as relative fluorescence units (RFU) or relative luminescence units (RLU), since there is no absolute value to which they are related. The corrected pixel (or grayscale) values for all the pixels in the area of interest representing the well, i.e., the subsection of the image frame, may be averaged to represent the light intensity at that location for the corresponding point in time.

The image integration module 190 integrates (i.e., combines, merges, and the like) the measurement results 178 associated with the image frames 186. By combining measurement results 178, the assay image acquisition system 150 may advantageously recreate a desired exposure time. For example, a 0.05 sec. exposure obtained at 120 fps corresponds to six image frames: 120 frames/sec.×0.05 sec.=6 image frames. To recreate a 0.05 sec. exposure, the image integration module 190 would, in this example, integrate six measurement results 178 to obtain an integrated measurement result 158. Where the measurement results 178 are numerical values, e.g., RFUs or RLUs, the image integration module 190 may, for example, add the six numerical values such that the integrated measurement result 158 is the sum of the six numerical values, e.g., the sum of the six RFUs or RLUs.

The output of the assay image acquisition process may depend on, for example, the duration of an exposure, the duration of the overall imaging period, or a desired number of exposures. The number of exposures, in this example, corresponds to the number of measurement results 178 for the individual samples of the assay sample 152. The assay image acquisition system 150 may use default values for the exposure time (e.g., 0.05 seconds), the imaging period (e.g., two minutes), or the number of exposures (i.e., sampling points or data points). Additionally or alternatively, a desired exposure time, a desired imaging period, or a desired number of data points may be received at the assay image acquisition system 150 as user input 164 from the image analysis system 162. The assay image acquisition system 150 may thus image the assay sample 152 based on the user input 164 received.

User input 164 received from the image analysis system 150 may correspond to the duration of the exposure, i.e., a particular exposure time. A user at the computing device 160 may input a desired exposure time, e.g., 0.05 sec., and the specified exposure time may be transmitted to the image integration module 190 as user input 164. The image integration module 190 may thus integrate a set of measurement results 178 based on the specified exposure time. As an example, a user may specify an exposure time of 0.05 sec., and at 120 fps, the image integration module 190 may integrate six image frames 186 to obtain an integrated measurement result 158 as discussed above. Similarly if the user specifies exposure times of 0.10 sec., 0.25 sec., and 0.50 sec., then at 120 fps, the image integration module 190 may integrate twelve image frames 186, thirty image frames 186, and sixty image frames 186 respectively to obtain integrated measurement results 158.

User input 164 received from the image analysis system 162 may also correspond to the duration of the imaging period, i.e., a particular imaging period time. A user at the computing device 160 may input a desired imaging period, e.g., two minutes (min.) and the specified imaging period may be transmitted to the assay image acquisition system 150 as user input 164. The camera control module 182 may thus instruct the camera 170 to image the assay sample 152 for the specified imaging period time. As an example, a user may specify an imaging period time of two minutes. At 120 fps, a two min. imaging period results in 14,400 image frames: 2 min.×60 sec./min.×120 frames/sec.=14,400 image frames. The image integration module 190 may integrate measurement results 178 associated with the image frames 186 based on a default or user-specified exposure time, e.g., 0.05 sec., which corresponds to 6 image frames/exposure. A 0.05 sec. exposure time corresponds to 2,400 artificially recreated exposures: 14,400 image frames÷6 frames/exposure=2,400 exposures. Accordingly the 2,400 exposures, in this example, may respectively correspond to 2,400 measurement results 178 (i.e., sampling points, data points).

Additionally or alternatively, user input 164 received at the assay image acquisition system 150 from the image analysis system 162 may correspond to a desired number of data points (sampling points)—i.e., a desired number of exposures. Where a user specifies a desired number of exposures, the assay image acquisition system 150 may automatically calculate the duration of the imaging period based on the user-specified number of exposures, the camera frame rate, and a default or user-specified exposure time. As an example, a user may instruct the assay image acquisition system 150 to obtain 800 exposures of the assay sample 152, i.e., 800 data points (sampling points). At 120 fps and an exposure time of 0.05 sec. (6 image frames/exposure), the duration of the imaging period is 40 seconds: (800 exposures×6 frames/exposure)÷120 frames/sec.=40 seconds.

It will be understood that the output of the image integration module 190 may be one or more integrated measurement results 158. The image integration module 190 may output a single integrated measurement result 158 for one of the locations in the assay sample 152, or the image integration module 190 may output a set of integrated measurement results 158 for one of the locations in the assay sample 152. The set of integrated measurement results 158 may include a time-based sequence of multiple integrated measurement results 158. Additionally the image integration module 190 may respectively output integrated measurement results 158 and sets of integrated measurement results 158 for multiple locations in the assay sample 152. For example, the image integration module 190 may output a data table of integrated measurement results 158 where the entries in the data table are integrated measurement results 158 respectively corresponding to the locations in the assay sample 152. The image integration module 190 may also output a time-based sequence of data tables containing integrated measurement results 158 also respectively corresponding to the locations in the assay sample 152.

Figure 2:
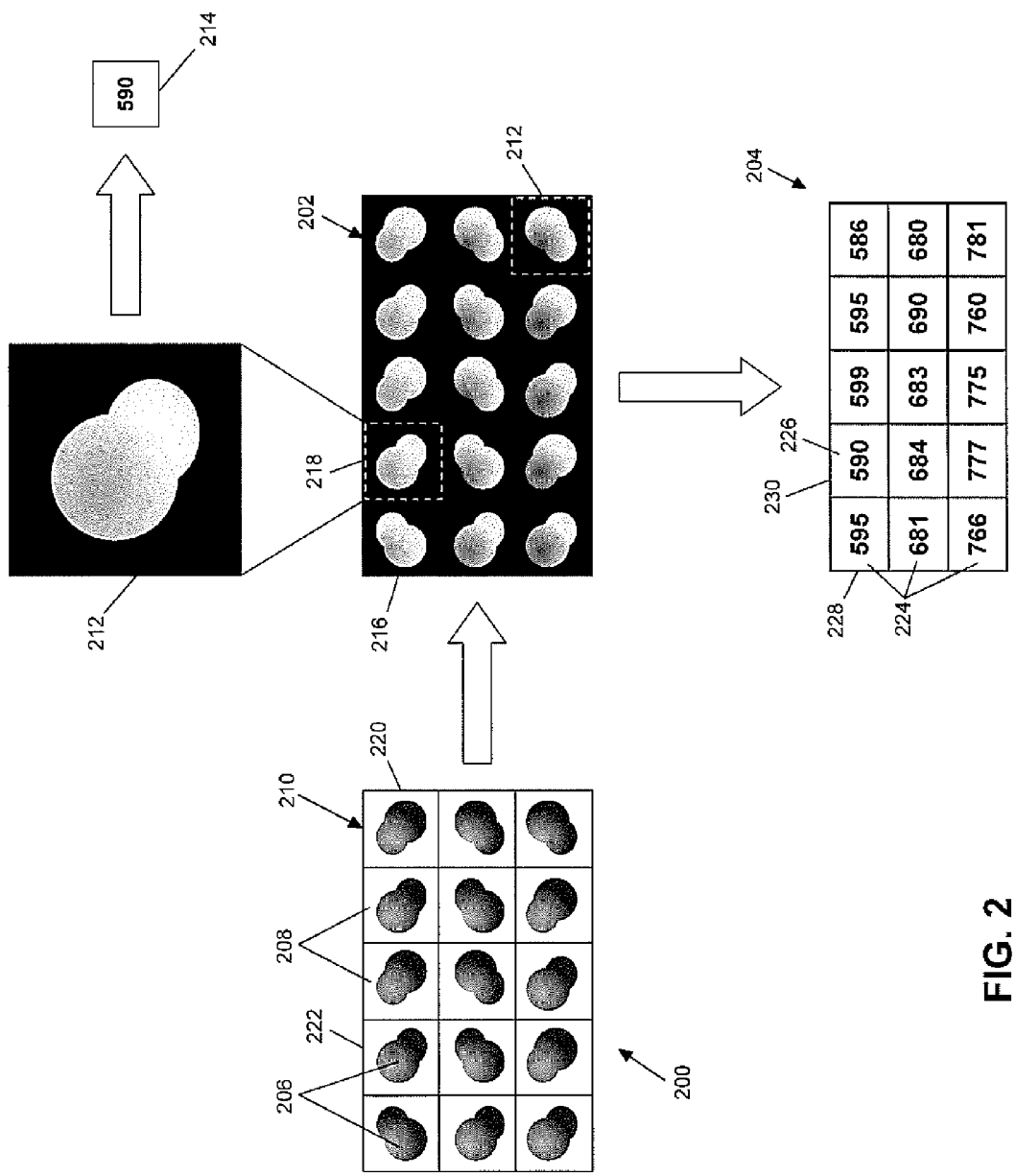
FIG. 2 is a representational diagram of an example of an assay sample, an example of an image frame, and an example of a data table.

Referring now to FIG. 2, a representational diagram of an example of an assay sample 200, an example of an image frame 202, and an example of a data table 204 is shown. An assay sample 200 may include multiple individual samples 206 arranged in respective wells 208 of a microplate 210. As discussed above with reference to FIG. 1, the camera 170 of the assay image acquisition system 150 may image an assay sample 152 to obtain an image stream 154. The frame grabber 174 may sample the image stream 154 to generate multiple image frames 156.

An example of an image frame 202 is shown in FIG. 2. The image frame 202, in this example, includes multiple subsections 212 that respectively correspond to the wells 208 of the microplate 210 of the assay sample 200. The image conversion module 188, in this example, may convert each subsection 212 of the image frame 202 to a numerical value 214 (e.g., RLU=590) that represents a property (e.g., light intensity) of the corresponding individual sample 206 in the assay sample 200. As mentioned above, the pixel data in the subsection 212 may be averaged to represent, e.g., the relative light or fluorescent intensity of the subsection 212 for that moment in time during the imaging period. The example subsection 212 shown in FIG. 2 is in the first row 216 and second column 218 of the image frame 202 and therefore corresponds to the well in the first row 220 and second column 222 of the microplate 210. The image conversion module 188 may generate a data table 204 for the image frame 202 where the numerical values for the subsections 212 of the image frame 202 correspond to individual entries 224 in the data table 204. The numerical value 224 for the example subsection 212 shown in FIG. 2 thus appears as the entry 226 in the first row 228 and second column 230 of the data table 204.

Figure 3:
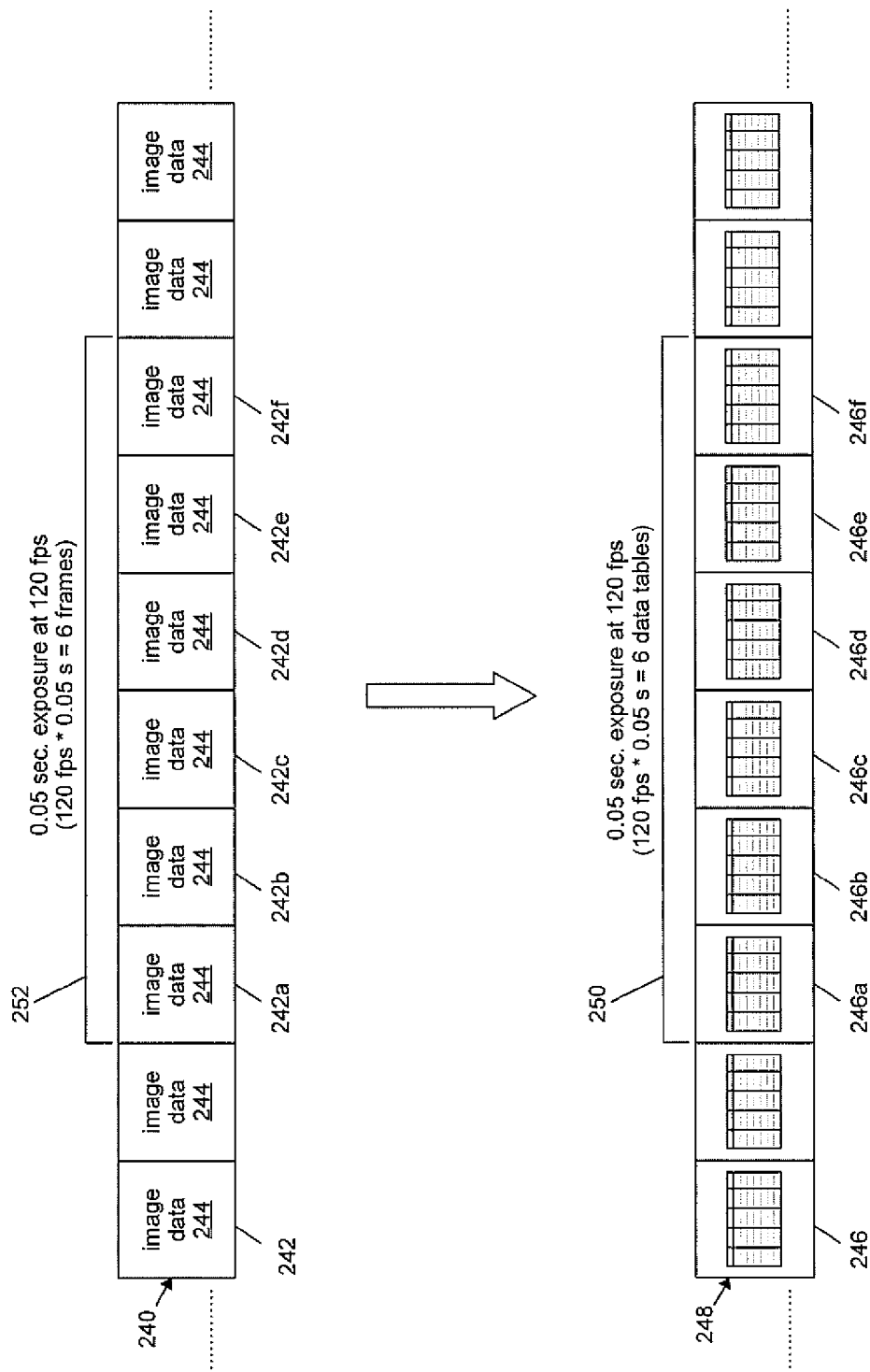
FIG. 3 is a block diagram of an example image conversion process for an example set of image frames.

With reference to FIG. 3, a block diagram of an example image conversion process for an example set 240 of image frames 242 is shown. The frame grabber 174 may sample the raw image data 172 of the image stream 154 from the camera 170 to obtain the set 240 of image frames 242. The image frames 242 may include image data 244 that may be raw image data or corrected image data as discussed above. The set 240 of image frames 242 may be arranged sequentially thus representing a time-based sequence of image frames 242.

In this example, the image conversion module 188 converts individual image frames 242 in the set 240 of image frames 242 to a data table 246 of numerical values, e.g., a data table of light intensity values (RLUs). The image conversion module 188 may convert each image frame 242 in the set 240 of image frames 242 to a data table 246 resulting in a set 248 of data tables 246. An example set 248 of data tables 246 is shown in FIG. 3. Each data table 246 in the set 248 of data tables 246, in this example, respectively corresponds to one of the image frames 242 in the set 240 of image frames 242. The set 248 of data tables 246 may also be arranged sequentially thus representing a time-based sequence of data tables 246.

Having obtained the set 248 of data tables 246, the image integration module 190 may integrate the numerical values of a subset 250 of data tables 246 to obtain an integrated numerical value, i.e., an integrated measurement result. Using the example above, a 0.05 sec. exposure at 120 fps corresponds to a subset 252 of six image frames 242a-e in the set 240 of image frames 242. The image integration module 190 may thus select a subset 250 of data tables 246 from the set 248 of data tables 246 where the subset 250 of data tables 246 include the six data tables 246a-e respectively corresponding to the six image frames 242a-e. The image integration module 190 may thus integrate the numerical values in the six data tables 246a-e to obtain the integrated numerical value.

Figure 4:
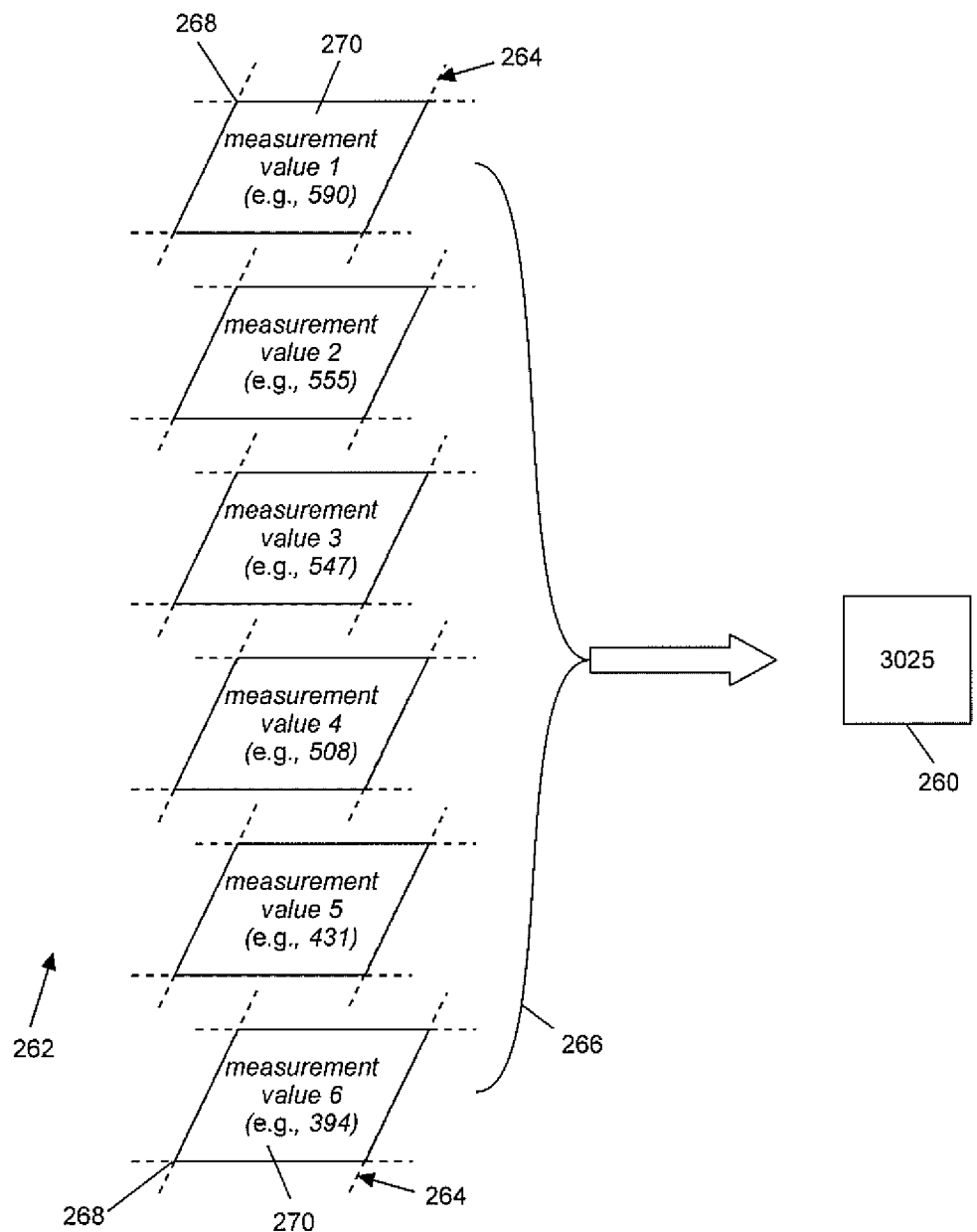
FIG. 4 is a representational diagram of an example integration process.

Referring to FIG. 4, a block diagram of an example integration process is shown. The example integration process shown in FIG. 4 determines an integrated measurement result 260 for a 0.05 sec. exposure at 120 fps. As mentioned above with reference to FIG. 3, the image integration module 190 may integrate a sequence of six measurement results to obtain the integrated measurement result 260 for the exposure.

As discussed above, the image conversion module 188 may respectively convert the set 240 of image frames 242 to a set 248 of respective data tables 246. The data tables 246 may include numerical values 224 (FIG. 2) that respectively correspond to subsections 212 of the image frame 202. In FIG. 4, a subset 262 of six data tables 264 is shown representing a sequence 266 of data tables 264. The sequence 266 of data tables 264 in FIG. 4 respectively correspond to the subset 252 of six image frames 242a-e in FIG. 3. The data tables 264, in this example, include an array 268 of numerical values 270. In FIG. 4, the sequence 266 corresponds to six numerical values 270 for a particular location (well) 208 in the assay sample 200 is shown: [590, 555, 547, 508, 431, 394].

The image integration module 190 may add the numerical values 270 in the sequence 266 to obtain the integrated numerical value 260, which, in this example, sums to 3025: 590+555+547+508+431+394=3025. In this example, the integrated numerical value 260 that equals 3025 represents the integrated measurement result for one of the locations in the assay sample 200 and corresponds to a 0.05 sec. exposure at 120 fps. The image integration module 190 may integrate additional sequences of measurement results to obtain a sequence of measurement results for a location in the assay sample 200 that correspond to a sequence of exposures of that location. The image integration module 190 may integrate more or less measurement results depending on the exposure time and camera frame rate. The image integration module 190 may, for example, integrate 12, 30, or 60 measurement results for respective exposure times of 0.10 sec., 0.25 sec., or 0.50 sec. at 120 fps.

As an example, the image integration module 190 may integrate the following six two-dimensional pixel arrays of averaged grayscale values for a subsection 212 of an image frame 202 to obtain an integrated measurement result:

| PIXEL ARRAY 1 | | |
|---|---|---|
| 230 | ... | 210 |
| ... | ... | ... |
| 250 | ... | 170 |
| PIXEL ARRAY 2 | | |
| 270 | ... | 250 |
| ... | ... | ... |
| 200 | ... | 150 |
| PIXEL ARRAY 3 | | |
| 210 | ... | 160 |
| ... | ... | ... |
| 180 | ... | 140 |
| PIXEL ARRAY 4 | | |
| 310 | ... | 350 |
| ... | ... | ... |
| 300 | ... | 350 |
| PIXEL ARRAY 5 | | |
| 370 | ... | 310 |
| ... | ... | ... |
| 330 | ... | 170 |
| PIXEL ARRAY 6 | | |
| 400 | ... | 450 |
| ... | ... | ... |
| 440 | ... | 410 |

The image integration module 190 may, in this example add the respective grayscale values in the six two-dimensional pixel arrays to obtain the grayscale values for the pixels in the integrated two-dimensional pixel array:

| INTEGRATED PIXEL ARRAY | | |
|---|---|---|
| 1790 | ... | 1730 |
| ... | ... | ... |
| 1700 | ... | 1390 |

Figure 5:
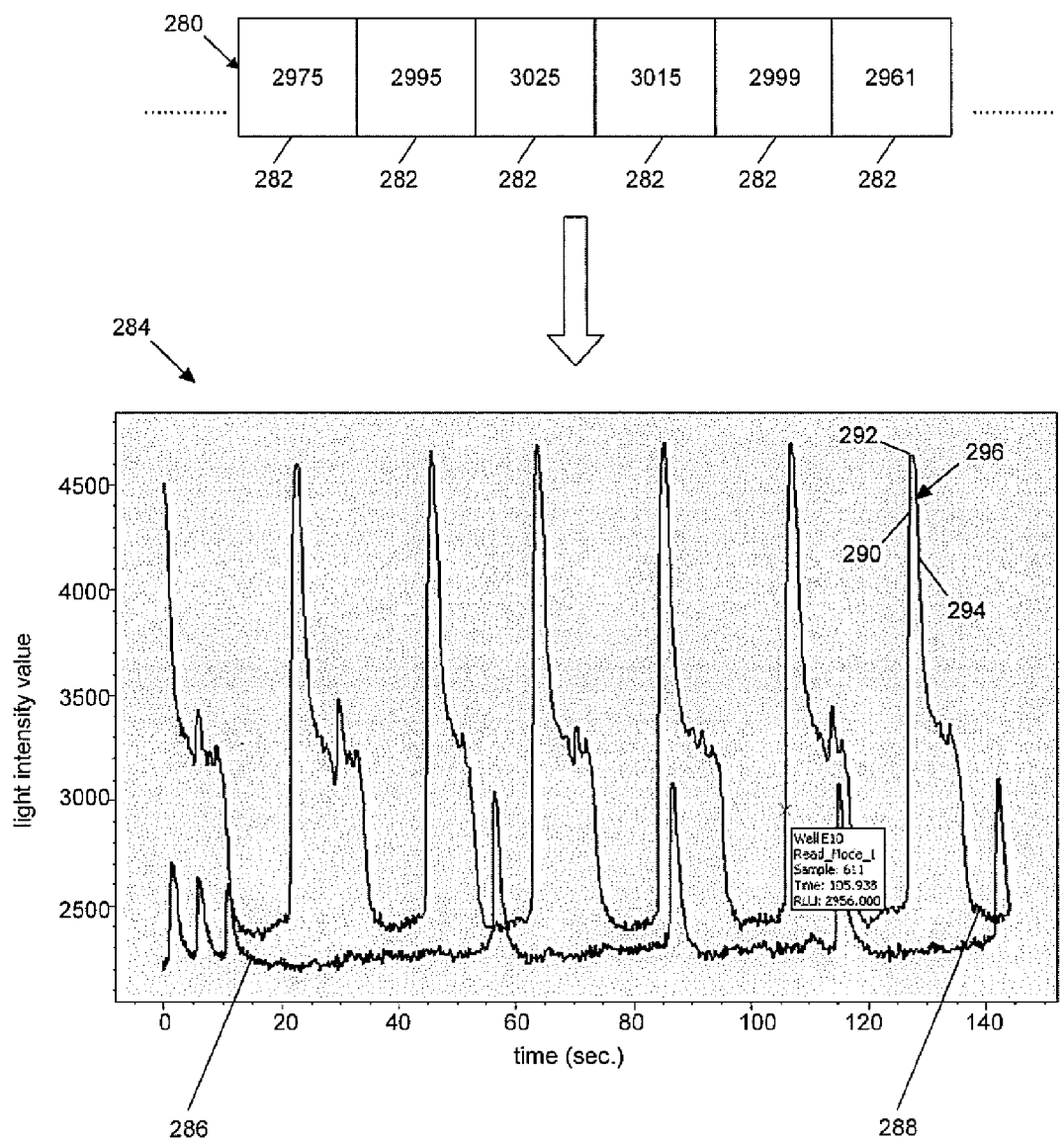
FIG. 5 is a diagram of an example sequence of integrated numerical values and an example chart graphing the sequence of integrated numerical values

With reference to FIG. 5, a diagram of an example sequence 280 of integrated numerical values 282 and an example chart 284 graphing the sequence 280 of integrated numerical values 282 is shown. The sequence 280 of integrated numerical values 282, in this example, corresponds to a particular image frame subsection 212 in a subset (sequence) of image frames 252 (FIG. 3) and by extension a particular location (well) 208 (FIG. 2) in the assay sample 200. Additionally, the sequence 280 of integrated numerical values 282 corresponds to multiple exposures of the assay sample 200. Individual integrated numerical values 282 in the sequence 280 of integrated numerical values 282 correspond to a particular exposure.

In FIG. 5, a sequence 280 of six integrated numerical values 282 is shown: [2975, 2995, 3025, 3015, 2999, 2961]. Continuing the example above, the sequence 280 of six integrated numerical values 282, in this example, correspond to six 0.05 sec. exposures at 120 fps, which corresponds to 36 total image frames: 120 frames/sec.×0.05 sec./exposure=6 frames/exposure×6 exposures=36 frames. The integrated numerical values 282 may correspond to a property of an individual sample 206 of the assay sample 200 such as, for example, light intensity.

Where the integrated measurement results 282 are numerical values as shown by way of example in FIG. 5, the integrated values 282 may thus be graphed as a time series to show how the value changes over time during the imaging period. In FIG. 5, the graph 284 includes two light intensity time series 286 and 288 for two respective locations (wells) 208 in an assay sample 200. As seen in FIG. 5, the graph 284 illustrates how the light intensity for the locations 208 in the assay sample 200 change during the imaging period of the assay.

A time series for a location 208 in the assay sample 200, in this example, may be referred to as a response curve. Each point on the response curves 286 and 288, in this example, corresponds to a light intensity value for the respective location 208 in the assay sample 200. Rising light intensities 290, peak light intensities 292, and falling light intensities 294 may represent action potentials 296 present in the response curves 286 and 288. The assay image acquisition system 150 may also advantageously provide a relatively high resolution response curve 296 due to the high number of data points resulting from the imaging period. A response curve 296 having a relatively high number of data points may thus also include a relatively high amount of detail. Accordingly researchers may analyze the response curves 286 and 288 to determine, for example, the response curve baseline and the rise time and decay time of action potentials 296 observed in the response curves 286 and 288.

As an example, an imaging period for an assay sample may be around 145 seconds. At 120 fps, imaging the assay sample would generate around 17,400 image frames: 145 sec.×120 frames/sec.=17,400 image frames. A default or user-specified exposure time may be used to integrate the measurement results associated with an exposure.

For an exposure time of 0.05 sec.—6 frames/exposure at 120 fps—the imaging period corresponds to 2,900 artificially recreated exposures: 17,400 frames÷6 frames/exposure=2,900 exposures. Where the measurement results are numerical values, the sequence of integrated numerical values may include 2,900 integrated measurement results, which provides a relatively high-resolution response curve having around 2,900 data points.

The assay image acquisition system 150 may also advantageously avoid gaps in the image acquisition process. As mentioned in the background section above, known assay imaging techniques may image an assay sample at intervals of 0.125 seconds with 0.05 seconds of the interval devoted to the exposure time and 0.075 seconds of the interval devoted to overhead thus resulting in 0.075 second gaps between exposures of the assay sample. In contrast the assay image acquisition system 150, in this example, advantageously avoids gaps in the image acquisition process by storing the entire image stream captured during the imaging period and artificially recreating exposures based on an exposure time. In this way, the assay image acquisition system may advantageously capture fast assay events that can occur during the gaps seen in known assay imaging techniques.

Figure 6:
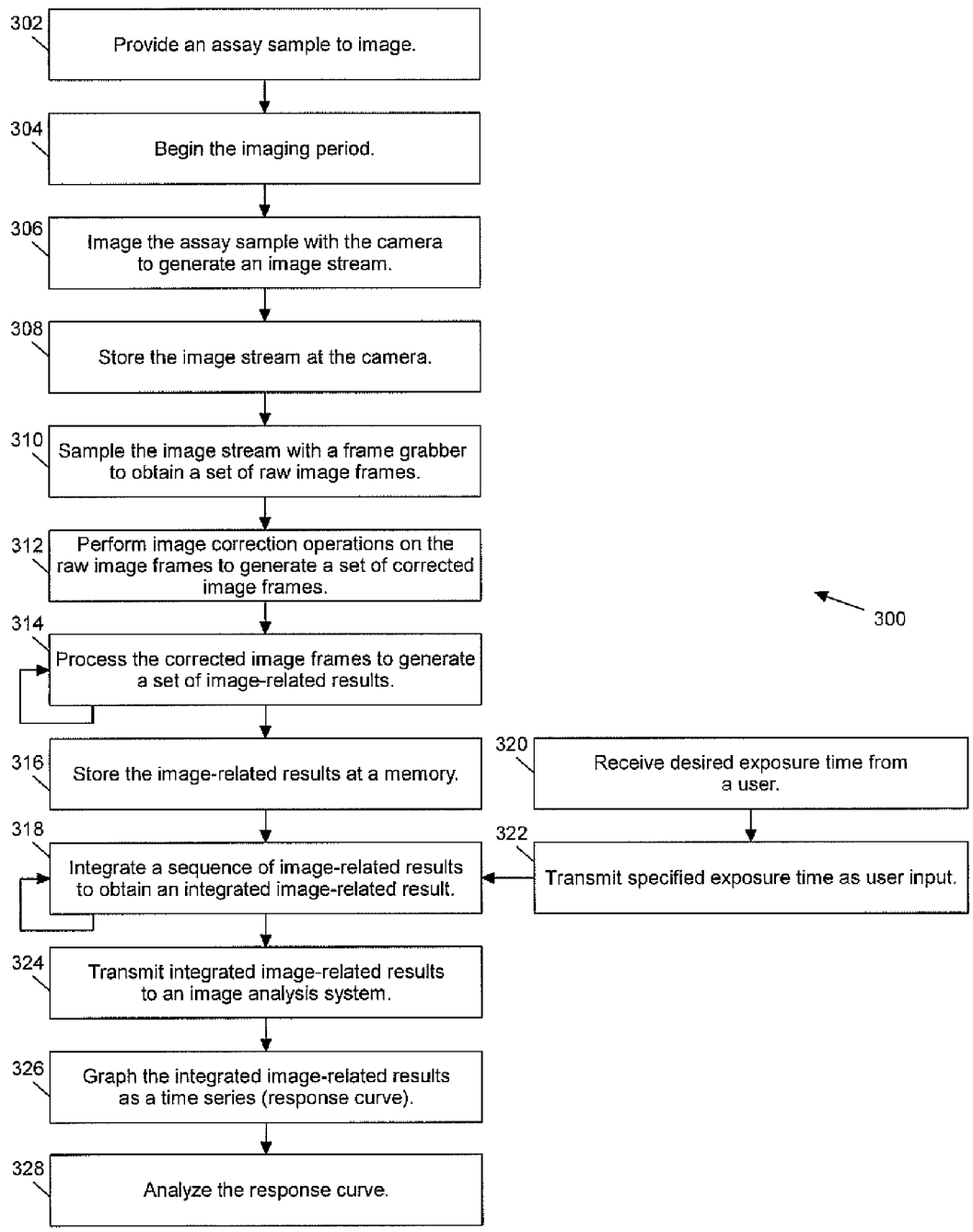
FIG. 6 is a flowchart of example method steps for imaging an assay sample.

Referring now to FIG. 6, a flowchart 300 of example method steps for imaging an assay sample is shown. First an assay sample to be imaged is provided (step 302). The assay sample may include a microplate having multiple wells where individual wells of the microplate hold individual samples. A camera begins an imaging period to image the assay sample (step 304) and generates an image stream (step 306) during the imaging period. The camera may be, for example, an ICCD camera. The camera may store the image stream during the imaging period (step 308), and a frame grabber may sample the image stream at a sampling rate to obtain a set of raw image frames (step 310). The sample rate may be, for example, 120 fps resulting in 120 image frames for each second of the imaging period. The image frames may include raw image data.

An image correction module may perform a set of image correction operations on the set of image frames (step 312) to obtain a set of corrected image frames. Image correction operations may include, for example, flat field correction, ADC offset, background subtraction, and the like. The corrected image frames may include corrected image data. An image conversion module may process the corrected image frames to generate a set of image-related results based on the image data in the image frames (step 314). An image-related result may be, for example, a numerical value corresponding to a property of an individual sample in the assay sample, e.g., a light intensity value corresponding to the luminescence of an individual sample in the assay sample.

Additionally the set of image-related results may be, for example, a data table having an array of numerical values where the numerical values in the data table correspond to subsections of an image frame. Accordingly the image conversion module may determine an image-related result for each subsection of an image frame. The image-related results may be stored at a memory (step 316).

An image integration module may then integrate a sequence of image-related results to obtain an integrated image-related result (step 318), e.g., an integrated light intensity value. The integrated image-related result may correspond to a particular exposure time, e.g., 0.05 seconds. The image integration module may integrate multiple sequences of image-related results to obtain multiple integrated image-related results.

A user may specify a desired exposure time (step 320), and the specified exposure time may be transmitted to the image integration module as user input (step 322). The image integration module may thus integrate a sequence of image-related results based on the user input received.

The integrated image-related results may be transmitted to an image analysis system (step 324) for further processing and analysis. For example, the image analysis system may graph a time series (response curve) corresponding to a sequence of integrated numerical values (step 326) to show how the integrated numerical value changes over time for an individual sample in the assay sample. The image analysis system may also analyze the response curve (step 328) to determine various response curve properties.

It will be understood and appreciated that one or more of the processes, sub-processes, and process steps described in connection with FIGS. 1-6 may be performed by hardware, software, or a combination of hardware and software on one or more electronic or digitally-controlled devices. The software may reside in a software memory (not shown) in a suitable electronic processing component or system such as, for example, one or more of the functional systems, devices, components, modules, or sub-modules schematically depicted in FIGS. 1-6. The software memory may include an ordered listing of executable instructions for implementing logical functions (that is, "logic" that may be implemented in digital form such as digital circuitry or source code, or in analog form such as analog source such as an analog electrical, sound, or video signal). The instructions may be executed within a processing module, which includes, for example, one or more microprocessors, general purpose processors, combinations of processors, digital signal processors (DSPs), field programmable gate arrays (FPGAs), or application-specific integrated circuits (ASICs). Further, the schematic diagrams describe a logical division of functions having physical (hardware and/or software) implementations that are not limited by architecture or the physical layout of the functions. The example systems described in this application may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., an assay image acquisition system in FIG. 1), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this document, computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access, i.e., volatile, memory (electronic); a read-only memory (electronic); an erasable programmable read only memory such as, for example, Flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used in this document means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electro-chemical, optical, wired, or wireless connections. The signal paths may also include additional systems, devices, components, modules, or sub-modules between the first and second system, device, component, module, or sub-module.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A computer-implemented method of imaging an assay sample having a set of individual samples using a camera, the computer-implemented method comprising:
   receiving a set of image frames by an image processing module, the set of image frames corresponds to an image stream of the assay sample obtained by the camera with a frame grabber;
   identifying a set of measurement results where individual measurement results in the set of measurement results are respectively associated with individual image frames in the set of image frames;
   selecting, based at least in part on an exposure time, a subset of measurement results from the set of measurement results; and
   combining individual measurement results in the subset of measurement results to obtain an integrated measurement result;
   wherein individual image frames in the set of image frames include an array of subsections, the subsections respectively correspond to individual samples in the assay sample;
the set of measurement results is a data table of numerical values; and
   individual values in the data table respectively correspond measurement results for individual subsections in the array of subsections.

2. The computer-implemented method of claim 1 further comprising:
   obtaining the image stream of the assay sample during an imaging period;
   sampling the image stream during the imaging period to obtain the image frames corresponding to the image stream; and
   processing the image frames during the imaging period to identify, at least in part, the set of measurement results.

3. The computer-implemented method of claim 1 wherein the individual image frames are converted based at least in part on image data respectively included in the individual image frames.

4. The computer-implemented method of claim 3 where combining individual measurement results in the subset of measurement results to obtain the integrated measurement result includes summing the values of the data table that respectively correspond to the individual measurement results in the subset of measurement results.

5. The computer-implemented method of claim 1 further comprising:
   selecting a plurality of subsets of measurement results from the set of measurement results where the plurality of subsets of measurement results are associated with one of the individual samples in the assay sample; and
   combining respective individual measurement results in each of the plurality of subsets of measurement results to obtain a set of integrated measurement results for the individual sample.

6. The computer-implemented method of claim 5 further comprising arranging individual integrated measurement results in the set of integrated measurement results in order, such that the set of integrated measurement results represents a time-based sequence of integrated measurement results for the individual sample.

7. The computer-implemented method of claim 5 further comprising obtaining a plurality of sets of integrated measurement results where the plurality of sets of integrated measurement results respectively correspond to a plurality of individual samples of the assay sample.

8. The computer-implemented method of claim 1 further comprising performing one or more image correction operations on individual image frames in the set of image frames to obtain a set of corrected image frames where individual measurement results in the set of measurement results respectively correspond to individual corrected image frames in the set of corrected image frames.

9. A system for imaging an assay sample having a set of individual samples using a camera, the system comprising:
   an image processing module that receives a set of image frames, the set of image frames corresponds to an image stream of the assay sample obtained by the camera and individual image frames in the set of image frames include an array of subsections respectively correspond to individual samples in the assay sample and respectively correspond to individual measurement results in a set of measurement results, which are presented as a data table of numerical values; where individual values in the data table respectively correspond measurement results for individual subsections in the array of subsections; and
   where the imaging processing module selects, based at least in part on an exposure time, a subset of measurement results from the set of measurement results and combines individual measurement results in the subset of measurement results to obtain an integrated measurement result.

10. The system of claim 9 where the image stream of the assay sample is obtained during an imaging period and further comprising a frame grabber that samples the image stream during the imaging period to obtain the image frames corresponding to the image stream such that the image processing module processes the image frames during the imaging period to obtain, at least in part, the set of measurement results.

11. The system of claim 9 where the image processing module comprises an image conversion module that converts individual image frames in the set of measurement results where the individual image frames are converted based at least in part on image data respectively included in the individual image frames.

12. The system of claim 11 where the image processing module further comprises an image integration module that sums the values of the data table that respectively correspond to the individual measurement results in the subset of measurement results.

13. The system of claim 9 where:
   the image processing module comprises an image integration module that selects a plurality of subsets of measurement results from the set of measurement results, the plurality of subsets of measurement results are associated with one of the individual samples in the assay sample; and
   where the image integration module respectively combines individual measurement results in each of the plurality of subsets of measurement results to obtain a set of integrated measurement results for the individual sample.

14. The system of claim 13 where individual integrated measurement results in the set of integrated measurement results are arranged in order such that the set of integrated measurement results represents a time-based sequence of integrated measurement results for the individual sample.

15. The system of claim 13 wherein the image integration module obtains a plurality of sets of integrated measurement results where the plurality of sets of integrated measurement results respectively correspond to a plurality of individual samples of the assay sample.

16. The system of claim 9 where the image processing module comprises an image correction module that performs one or more image correction operations on individual image frames in the set of image frames to obtain a set of corrected image frames where individual measurement results in the set of measurement results respectively correspond to individual corrected image frames in the set of corrected image frames.

17. A computer-implemented method of imaging an assay sample having a set of individual samples using a camera, the computer-implemented method comprising:
   obtaining an image stream of the assay sample with an image processing module of the camera during an imaging period;
   sampling the image stream during the imaging period to obtain a set of image frames, the image frames correspond to the image stream;
   performing one or more image correction operations on individual image frames in the set of image frames by an image correction module to obtain a set of corrected image frames;
   converting the set of corrected image frames by an image conversion module to obtain a set of measurement results;
   selecting a subset of measurement results from the set of measurement results based, at least in part, on an exposure time; and
   combining individual measurement results in the subset of measurement results by an image integration module to obtain an integrated measurement result;
   wherein individual image frames in the set of image frames include an array of subsections, the subsections respectively correspond to individual samples in the assay sample; the set of measurement results is a data table of numerical values; and
   individual values in the data table respectively correspond measurement results for individual subsections in the array of subsections.

18. The computer-implemented method of claim 17 where:
   individual image frames in the set of image frames include an array of subsections;
   individual subsections in the array of subsections respectively correspond to individual samples in the assay sample;
the set of measurement results is a data table of numerical values; and
   individual values in the data table respectively correspond to individual subsections in the array of subsections and individual samples in the assay sample.

* * * * *